US009161939B2

(12) United States Patent
Mitton-Fry et al.

(10) Patent No.: US 9,161,939 B2
(45) Date of Patent: Oct. 20, 2015

(54) PYRROLO[2,3-D]PYRIMIDINE COMPOUNDS

(71) Applicant: Zoetis LLC, Florham Park, NJ (US)

(72) Inventors: Mark J. Mitton-Fry, Clinton, CT (US); Pamela J. Berlinski, Parchment, MI (US); Matthew J. Birchmeier, Kalamazoo, MI (US); Jerry W. Bowman, Lawton, MI (US); Andrea Joy Gonzales, Kalamazoo, MI (US); Steven Glenn Kamerling, Kalamazoo, MI (US); Donald Wayne Mann, Jewett City, CT (US)

(73) Assignee: Zoetis Services LLC, Florham Park, NJ (US)

( * ) Notice: Subject to any disclaimer, the term of this patent is extended or adjusted under 35 U.S.C. 154(b) by 0 days.

(21) Appl. No.: 14/619,195

(22) Filed: Feb. 11, 2015

(65) Prior Publication Data

US 2015/0148357 A1 May 28, 2015

Related U.S. Application Data

(62) Division of application No. 13/360,963, filed on Jan. 30, 2012, now Pat. No. 8,987,283, which is a division of application No. 12/542,451, filed on Aug. 17, 2009, now Pat. No. 8,133,899.

(60) Provisional application No. 61/090,371, filed on Aug. 20, 2008.

(51) Int. Cl.
*A01N 43/90* (2006.01)
*A61K 31/519* (2006.01)
*C07D 487/04* (2006.01)

(52) U.S. Cl.
CPC ............ *A61K 31/519* (2013.01); *C07D 487/04* (2013.01)

(58) Field of Classification Search
None
See application file for complete search history.

(56) References Cited

U.S. PATENT DOCUMENTS

| | | | |
|---|---|---|---|
| 3,037,980 A | 6/1962 | Hitchings et al. |
| 3,670,079 A | 6/1972 | Patanelli et al. |
| 4,456,464 A | 6/1984 | Lee et al. |
| 4,526,608 A | 7/1985 | Lee |
| 4,590,282 A | 5/1986 | Henrick |
| 4,879,309 A | 11/1989 | Doll et al. |
| 4,933,339 A | 6/1990 | Sharma |
| 4,997,936 A | 3/1991 | Christensen et al. |
| 5,134,123 A | 7/1992 | Branca et al. |
| 5,356,903 A | 10/1994 | Eissenstat et al. |
| 5,389,509 A | 2/1995 | Maskasky |
| 5,496,946 A | 3/1996 | Akimoto et al. |
| 5,686,457 A | 11/1997 | Traxler et al. |
| 6,080,747 A | 6/2000 | Uckun et al. |
| 6,136,595 A | 10/2000 | Ihle et al. |
| 6,180,636 B1 | 1/2001 | Traxler et al. |
| 6,187,552 B1 | 2/2001 | Roberds et al. |
| 6,310,063 B1 | 10/2001 | Ge et al. |
| 6,506,762 B1 | 1/2003 | Horvath et al. |
| 6,552,192 B1 | 4/2003 | Hanus et al. |
| 6,635,762 B1 | 10/2003 | Blumenkopf et al. |
| 6,890,929 B2 | 5/2005 | Blumenkopf et al. |
| 6,965,027 B2 | 11/2005 | Flanagan et al. |
| 7,192,963 B2 | 3/2007 | Blumenkopf et al. |
| 7,244,729 B2 | 7/2007 | Bold et al. |
| 7,250,420 B2 | 7/2007 | Changelian |
| 7,253,166 B2 | 8/2007 | Ding et al. |
| 7,253,286 B2 | 8/2007 | Funahashi et al. |
| 7,301,023 B2 | 11/2007 | Flanagan et al. |
| 7,432,370 B2 | 10/2008 | Wilcox et al. |
| 7,465,726 B2 | 12/2008 | Ahmed et al. |
| 7,569,569 B2 | 8/2009 | Blumenkopf et al. |
| 7,601,727 B2 | 10/2009 | Blumenkopf et al. |
| 2005/0159433 A1 | 7/2005 | Changelian et al. |
| 2005/0159434 A1 | 7/2005 | Flanagan et al. |
| 2005/0171128 A1 | 8/2005 | Blumenkopf et al. |

FOREIGN PATENT DOCUMENTS

| | | |
|---|---|---|
| EP | 0 334 636 | 9/1989 |
| EP | 0 682 027 | 11/1995 |
| EP | 0 795 556 | 9/1997 |
| GB | 915303 | 1/1963 |
| GB | 915304 | 1/1963 |
| WO | 95/19774 | 7/1995 |
| WO | 96/40142 | 12/1996 |
| WO | 97/02262 | 1/1997 |
| WO | 97/02266 | 1/1997 |
| WO | 97/13771 | 4/1997 |
| WO | 97/18212 | 5/1997 |
| WO | 97/27199 | 7/1997 |
| WO | 97/28161 | 8/1997 |
| WO | 97/32879 | 9/1997 |
| WO | 97/49706 | 12/1997 |

(Continued)

OTHER PUBLICATIONS

Kisseleva, "Signaling through the JAK/STAT pathway, recent advances and future challenges", Gene, 285:1-24, 2002.
Yamaoka, "The Janus kinases (Jaks)", Genome Biology, 5(12):253-253.6, 2004.
PCT International Search Report, PCT/IB2009/053514, 2009.
Traxler et al., "4-(Phenylamino)pyrrolopyrimidines: Potent and Selective, ATP Site Directed Inhibitors of the EGF-Receptor Protein Tyrosine Kinase", J. Med. Chem., 39:2285-2292, 1996.
Johnston et al., "Phosphorylation and activation of the Jak-3 Janus kinase in response to interleukin-2", Nature, 370:151-153, 1994.
Russell et al., "Interaction of IL-2Rbeta and gammac Chains with Jak1 and Jak3: Implications for XSCID and XCID", Science, 266(5187):1042-1045, 1994.
Ihle, "The Janus Protein Tyrosine Kinase Family and Its Role in Cytokine Signaling", Adv. Immunology, 60:1-35, 1995.

(Continued)

*Primary Examiner* — Jeffrey H Murray
(74) *Attorney, Agent, or Firm* — Paul M. Misiak; Barbara L. Renda

(57) ABSTRACT

Described herein is pyrrolo{2,3-d}pyrimidine compounds, their use as Janus Kinase (JAK) inhibitors, pharmaceutical compositions containing this compounds, and methods for the preparation of these compounds.

10 Claims, 3 Drawing Sheets

(56) References Cited

FOREIGN PATENT DOCUMENTS

| WO | 98/02437 | 1/1998 |
|---|---|---|
| WO | 98/02438 | 1/1998 |
| WO | 98/07726 | 2/1998 |
| WO | 98/23613 | 6/1998 |
| WO | 98/33798 | 8/1998 |
| WO | 99/51599 | 10/1999 |
| WO | 99/61428 | 12/1999 |
| WO | 99/65908 | 12/1999 |
| WO | 99/65909 | 12/1999 |
| WO | 00/00202 | 1/2000 |
| WO | 00/10981 | 3/2000 |
| WO | 00/17203 | 3/2000 |
| WO | 01/42246 | 6/2001 |
| WO | 02/00661 | 1/2002 |
| WO | 2006/069080 | 6/2006 |
| WO | 2006/116713 | 11/2006 |
| WO | 2008/089307 | 7/2008 |
| WO | 2008/089310 | 7/2008 |

OTHER PUBLICATIONS

Ihle, "The Janus protein tyrosine kinases in hemoatopoietic cytokine signaling", Semin. Immunology, 7(4):247-254, 1995.
Musso et al., "Regulation of JAK3 Expression in Human Monocytes: Phosphorylation in Response to Interleukins 2, 4, and 7", J. Exp. Med., 181(4):1425-1431, 1995.
Kirken et al., "Activation of JAK3, but Not JAK1, is Critical for IL-2-Induced Proliferation and STAT5 Recruitment by a COOH-terminal Region of the IL-2 Receptor Beta-Chain", Cytokine, 7(7):689-700, 1995.
Malabarba et al., "Activaton of JAK3. but Not JAK1, Is Critical to Interleukin-4 (IL4) Stimulated Proliferation and Requires a Membrane-proximal Region of IL4 Receptor alpha", J. Biol. Chem., 270:9630-9637, 1995.
Hanke et al., "Role of tyrosine kinases in lymphocyte activation: Targets for drug intervention", Inflamm. Res., 44(9):357-371, 1995.
Eynon et al., "Disruption of Cytokine Signaling in Lymphoid Development: Unique Contributions of the Common Cytokine Gamma Chain and the Jak3 Kinase", J. Interferon Cytokine Res., 16(9):677-684, 1996.
Oakes et al., "Signaling via IL-2 and IL-4 in JAK3-Deficient Severe Combined Immunodeficiency Lymphocytes: JAK3-Dependent and Independent Pathways", Immunity, 5(6):605-615, 1996.
Notarangelo et al., "Severe Combined Immune Deficiency Due to Defects of the JAK3 Tyrosine Kinase", Progress in Immunodeficiency VI:61-68, 1996.
Thomis and Berg, "Peripheral Expression of Jak3 is Required to Maintain T Lymphocyte Function", J. Exp. Med., 185(2):197-206, 1997.
Nelson et al., "Requirement for an initial signal from the membrane-proximal region of the interleukin 2 receptor gamma(c) chain for Janus kinase activation leading to T cell proliferation", Proc. Natl. Acad. Sci. USA, 94(5):1878-1883, 1997.
Baird et al., "T cell development and activation in Jak3-deficient mice", J. Leukocyte Biol., 63(6):669-677, 1998.
Liu et al., "JAK/STAT signaling by cytokine receptors", Curr. Opin. Immunol., 10(3):271-278, 1998.
Leonard and O'Shea, "JAKS and STATS: Biological Implications", Annu. Rev. Immunol., 16:293-322, 1998.
Candotti et al., "Severe combined immune deficiencies due to defects of the common gamma chain—JAK3 signaling pathway", Springer Semin. Immunopathol., 19(4):401-415, 1998.
Malaviya et al., "Targeting Janus Kinase 3 in Mast Cells Prevents Immediate Hypersensitivity Reactions and Anaphylaxis", J. Biol, Chem., 274(38):27028-27038, 1999.
Thomis et al., "The Jak Family Tyrosine Kinase Jak3 Is Required for IL-2 Synthesis by Naive/Resting CD4+ T Cells", J. Immunol., 163(10):5411-5417, 1999.
Chen et al., "Advances in Cytokine Signaling: The Role of Jaks and STATs" Transplanaton Proc., 31(3):148-1487, 1999.

Moriggi et al., "Stat5 Activation is Uniquely Associated with Cytokine Signaling in Peripheral T Cells", Immunity, 11:225-230, 1999.
Wang et al., "JAK3, STAT, and MAPK Signaling Pathways as Novel Molecular Targets for the Tyrphostin AG-490 Regulation of IL-2-Mediated T Cell Response", J. Immunol., 162(7):3897-3904, 1999.
Sudbeck et al., "Structure-based Design of Specific Inhibitors of Janus Kinase 3 as Apoptosis-including Antileukemic Agents", Clin. Cancer Res., 5(6):1569-1582, 1999.
Uckun et al., "In Vivo Toxicity and Pharmacokinetic Features of the Janus Kinase 3 Inhibitor WHI-P131 [4-(4'Hydroxyphenyl)-Amino-6,7-Dimethoxyquinazoline]", Clin. Cancer Res., 5(10):2954-2962, 1999.
Sudbeck and Uckun, "Recent advances in JAK3 kinase inhibitors", IDrugs, 2(10):1026-1030, 1999.
Malaviya and Uckun, "Genetic and Biochemical Evidence for a Critical Role of Janus Kinase (JAK)-3 in Mast Cell-Mediated Type I Hypersensitivity Reactions", Biochem. Biophys. Res. Commun., 257(3):807-813, 1999.
Trieu et al., "A Specific Inhibitor of Janus Kinase-3 Increases Survival in a Transgenic Mouse Model of Amyotrophic Lateral Sclerosis", Biochem. Biophys. Res. Commun., 267(1):22-25, 2000.
Li et al., "Blocking the Common gamma-Chain of Cytokine Receptors Induces T Cell Apoptosis and Long-Term Islet Allograft Survival", J. Immunol., 164(3):1193-1199, 2000.
Malaviya et al., "Treatment of Allergic Asthma by Targeting Janus Kinase 3-Dependent Leukotriene Synthesis in Mast Cells with 4-(3', 5'-Dibromo-4'-hydroxyphenyl)amino-6,7-dimethoxyquinazoline (WHI-P97)", J. Pharmacol. Exp. Ther., 295(3):912-926, 2000.
Ghosh et al., "4-[(3-Bromo-4-hydroxyphenyl)amino]-6,7-dimethoxyquinazolin-1-ium chloride methanol solvate and 4-[(3-hydroxyphenyl)amino]-6,7-di-methoxy-1-quinazolinium chloride", Acta Cryst. SectC: Cryst. Struct. Commun., C57:76-78, 2001.
Sudbeck et al., "An inhibitor of Janus kinase 3: 4-(4-hydroxyphenylamino)-6,7-dimethoxyquinazolin-1-ium chloride methanol solvate", Acta Cryst. SectC: Cryst. Stud. Commun., C56:1282-1283, 2000.
Traxler et al., "Protein tyrosine kinase inhibitors in cancer treatment", Exp. Opin. Ther. Patents, 7(6):571-588, 1997.
Iwamura et al., "Quantitative aspects of the receptor binding of cytokinin agonists and antagonists", J. Med. Chem., 26(6):838-844, 1983.
Mass, "The HER Receptor Family: A Rich Target for Therapeutic Development", Int. J. Radiation Oncology Biol. Phys., 58(3):932-940, 2004.
Fabbro et al., "Protein kinases as targets for anticancer agents: from inhibitors to useful drugs", Pharmacology & Therapeutics, 93:79-98, 2002.
Simone, Cecil Textbook of Medicine, edited by Bennett, J.C., and Plum F., 20th edition, vol. 1, pp. 1004-1010, 1996.
Shouda et al., "Induction of the cytokine signal regulator SOCS3/CIS3 as a therapeutic strategy for treating inflammatory arthritis", J. Clin. Invest., 108(12)1781-1788, 2001.
Aringer et al., "Janus kinases and their role in growth and disease", Life Sciences, 64(24):2173-2186, 1999.
The MDAdvice.com entry for Asthma http://www.mdadvice.com/topics/asthma/info/1.htm downloaded fom the Internet Mar. 5, 2003.
The Medline Medical Encyclopedia entry for Psoriasis http://www.nlm.nih.gov/medlineplus/ency/article/000434.htm downloaded from the Internet Mar. 5, 2003.
Illustrated Health Encyclopedia entry for Crohn's disease Prevention http://www.austin360.com/shared/health/adam/ency/article/000249prv.html downloaded from the Internet Mar. 5, 2003.
Columbia University College of P & S Complete Home Medical Guide entry for Arthritis Prevention http://cpmcnet.columbia.edu/texts/guide/hmg25_0006.html downloaded from the Internet Mar. 5, 2003.
Bolen and Brugge, "Leukocyte Protein Tyrosine Kinases: Potential Targets for Drug Discovery", Annu. Rev. Immunol., 15:371-404, 1997.

PYRROLO[2,3-D]PYRIMIDINE COMPOUNDS

CROSS-REFERENCE TO RELATED APPLICATIONS

This application is a divisional of U.S. patent application Ser. No. 13/360,963 filed Jan. 30, 2012, now allowed; which is a divisional of U.S. patent application Ser. No. 12/542,451 filed Aug. 17, 2009, now granted as U.S. Pat. No. 8,133,899, which claims the benefit of priority to U.S. Provisional Application No. 61/090,371 filed Aug. 20, 2008.

FIELD OF THE INVENTION

Described herein is N-methyl(4-(methyl(7H-pyrrolo[2,3-d]pyrimidin-4-yl)amino)cyclohexyl)methanesulfonamide, its analogues, their use as Janus Kinase (JAK) inhibitors, pharmaceutical compositions containing these compounds, and methods for the preparation of these compound.

BACKGROUND OF THE INVENTION

Protein kinases are families of enzymes that catalyze the phosphorylation of specific residues in proteins, broadly classified into tyrosine and serine/threonine kinases. Inappropriate kinase activity, arising from mutation, over-expression, or inappropriate regulation, dys-regulation or de-regulation, as well as over- or under-production of growth factors or cytokines has been implicated in many diseases, including but not limited to cancer, cardiovascular diseases, allergies, asthma and other respiratory diseases, autoimmune diseases, inflammatory diseases, bone diseases, metabolic disorders, and neurological and neurodegenerative disorders such as Alzheimer's disease. Inappropriate kinase activity triggers a variety of biological cellular responses relating to cell growth, cell differentiation, survival, apoptosis, mitogenesis, cell cycle control, and cell mobility implicated in the aforementioned and related diseases.

Thus, protein kinases have emerged as an important class of enzymes as targets for therapeutic intervention. In particular, the JAK family of cellular protein tyrosine kinases (JAK-1, JAK-2, JAK-3, and Tyk-2) play a central role in cytokine signaling (Kisseleva et al, Gene, 2002, 285, 1; Yamaoka et al. Genome Biology 2004, 5, 253)). Upon binding to their receptors, cytokines activate JAK which then phosphorylate the cytokine receptor, thereby creating docking sites for signaling molecules, notably, members of the signal transducer and activator of transcription (STAT) family that ultimately lead to gene expression. Numerous cytokines are known to activate the JAK family.

Accordingly, there remains a need for alternative compounds that effectively inhibit JAK enzymes, including JAK-1, JAK-2, JAK-3, and/or Tyk-2.

SUMMARY OF THE INVENTION

The present invention provides a compound of formula I:

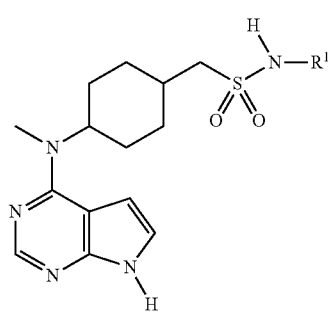

I or a pharmaceutically acceptable salt thereof wherein $R^1$ is —$C_{1-4}$alky, optionally substituted with hydroxy.

Specifically, a compound of formula I wherein $R^1$ is methyl.

Specifically, a compound of formula I wherein $R^1$ is ethyl or cyclobutyl.

In another aspect, the present invention also provides:

pharmaceutical compositions which comprise a pharmaceutically acceptable carrier and a compound of formula I, methods for controlling or treating a disorder or condition selected from organ transplant rejections, lupus, multiple sclerosis, rheumatoid arthritis, psoriasis, cancer, osteoarthritis, and diabetes by administering to a mammal in need a therapeutically effective amount of a compound of formula I or a pharmaceutically acceptable salt thereof, methods for controlling or treating a disorder or condition selected from diabetes, cancer, autoimmune thyroid disorders, ulcerative colitis, Crohn's disease, dry eyes, Alzheimer's disease, leukemia, and other indications where immunosuppression or immunomodulation would be desirable by administering to a mammal in need a therapeutically effective amount of a compound of formula I or a pharmaceutically acceptable salt thereof, methods for controlling or treating a disorder or condition selected from allergic reaction including allergic dermatitis, eczema, atopic dermatitis, pruritus and other pruritic conditions and inflammatory disease such as bowel disease in mammal by administering to a mammal in need a therapeutically effective amount of a compound of formula I or a pharmaceutically acceptable salt thereof, methods for controlling or treating a disorder or condition selected from Asthma and other obstructive airways diseases, including chronic or inveterate asthma, late asthma, airway hyper-responsiveness, bronchitis, bronchial asthma, allergic asthma, intrinsic asthma, extrinsic asthma, dust asthma, recurrent airway obstruction, and chronic obstruction pulmonary disease by administering to a mammal in need a therapeutically effective amount of a compound of formula I or a pharmaceutically acceptable salt thereof, methods for the inhibition of protein tyrosine kinases or JAK-1, JAK-2, JAK-3 and/or Tyk-2 by administering to a mammal in need of a therapeutically effective amount of a compound of formula I or a pharmaceutically acceptable salt thereof, methods for the inhibition of protein tyrosine kinases or JAK-1, JAK-2, JAK-3 and/or Tyk-2 by administering to a mammal in need of a therapeutically effective amount of a compound of formula I or a pharmaceutically acceptable salt thereof, and methods for the preparation of compounds of the present invention.

DETAILED DESCRIPTION

Figure 1:
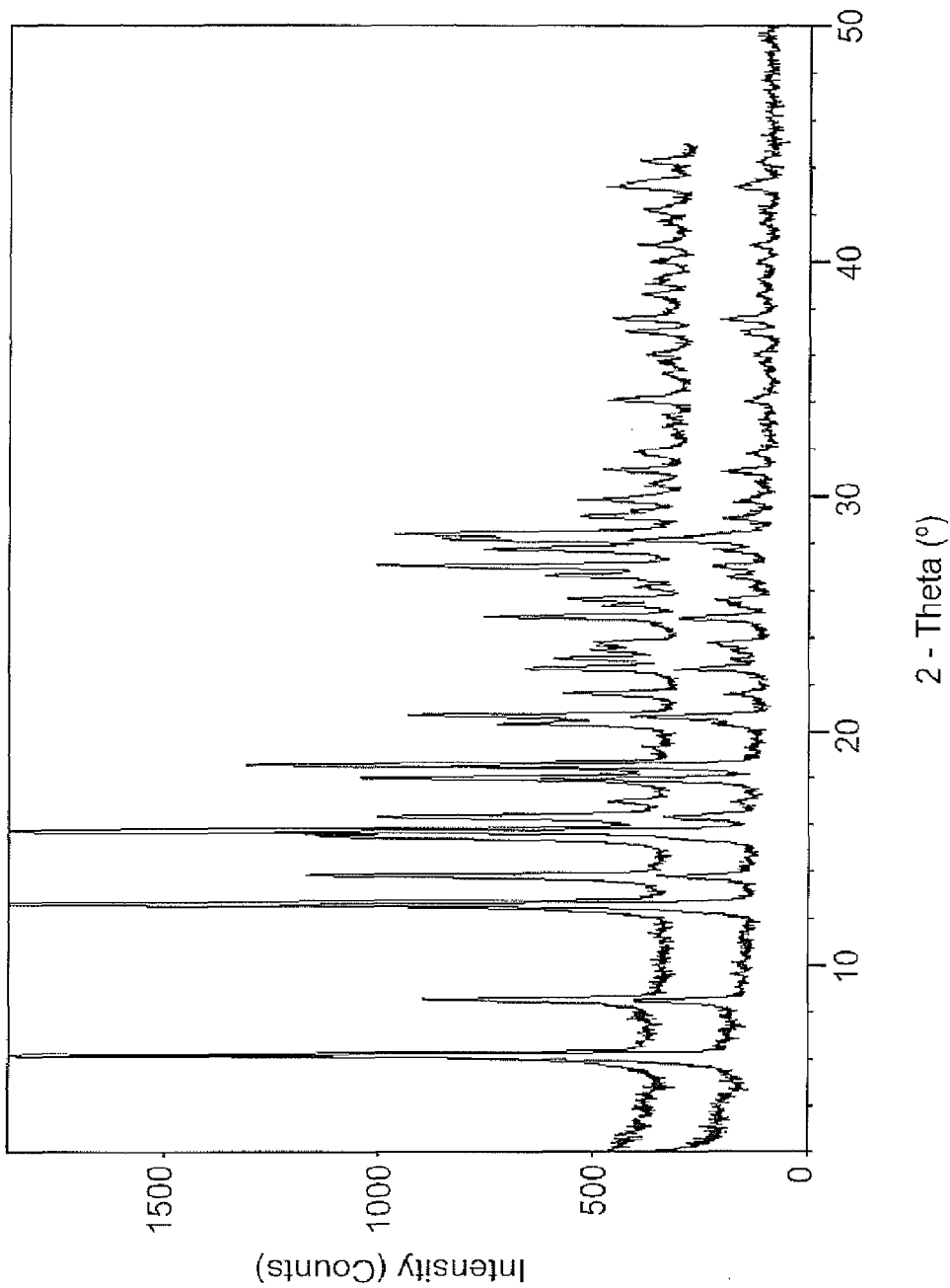
FIG. 1 is a characteristic X-ray powder diffraction pattern of N-methyl-1-{trans-4-[methyl(7H-pyrrolo[2,3-d]pyrimidin-4-yl)amino]cyclohexyl}methanesulfonamide maleic acid salt (Form A).

With respect to the above compound, and throughout the application and claims, the following terms have the meanings defined below.

The term "mammal" refers to human or animals including livestock and companion animals. The phrase "companion animal" or "companion animals" refers to animals kept as pets. Examples of companion animals include cats, dogs, and horses. The term "livestock" refers to animals reared or raised in an agricultural setting to make products such as food or fiber, or for its labor. In some embodiments, livestock are suitable for consumption by mammals, for example humans. Examples of livestock animals include mammals, such as cattle, goats, horses, pigs, sheep, including lambs, and rabbits, as well as birds, such as chickens, ducks and turkeys.

The term "controlling", "treating" or "treatment" of a disease includes: (1) preventing the disease, i.e. causing the clinical symptoms or signs of the disease not to develop in a mammal that may be exposed to or predisposed to the disease but does not yet experience or display symptoms/signs of the disease; (2) inhibiting the disease, i.e., arresting or reducing the development of the disease or its clinical symptoms/signs; or (3) relieving the disease, i.e., causing regression of the disease or its clinical symptoms/signs.

The term "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The term "approximately" if used in defining a peak in an X-ray powder diffraction pattern is defined as the stated 2-theta value±0.2 degree 2-theta. Any determination of whether a crystalline form is the Form A polymorph and encompassed by the claims should be interpreted in light of the variability in this test.

"Pharmaceutically acceptable" means suitable for use in mammals, companion animals or livestock animals.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-4}$ alkyl refers to alkyl of one to four carbon atoms, inclusive.

The term alkyl refers to straight, branched and a cyclic saturated monovalent hydrocarbon groups, but reference to an individual radical such as "propyl" embraces only the straight chain radical, a branched chain isomer such as "isopropyl" or a cyclic isomer such as cyclopropylmethyl or cyclopentyl being specifically referred to.

Compounds that have the same molecular formula but differ in the nature or sequence of bonding of their atoms or the arrangement of their atoms in space are termed "isomers". Isomers that differ in the arrangement of their atoms in space are termed "stereoisomers". It will be appreciated by those skilled in the art that the compound of formula I can exist as cis- and trans-achiral diastereomers. Specifically, the present invention provides a compound of formula IA, which has the chemical name N-methyl-1-{trans-4-[methyl(7H-pyrrolo[2,3-d]pyrimidin-4-yl)amino]cyclohexyl}methanesulfonamide,

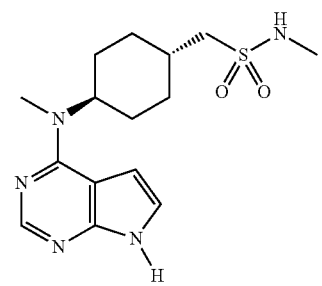

IA or a pharmaceutically acceptable salt thereof.

Included within the scope of the described compounds are all isomers (e.g. cis-, trans-, or diastereomers) of the compounds described herein alone as well as any mixtures. All of these forms, including enantiomers, diastereomers, cis, trans, syn, anti, solvates (including hydrates), tautomers, and mixtures thereof, are included in the described compounds.

Stereoisomeric mixtures, e.g. mixtures of diastereomers, can be separated into their corresponding isomers in a known manner by means of suitable separation methods. Diastereomeric mixtures for example may be separated into their individual diastereomers by means of fractionated crystallization, chromatography, solvent distribution, and similar procedures. This separation may take place either at the level of one of the starting compounds or in a compound of formula I itself. Enantiomers may be separated through the formation of diastereomeric salts, for example by salt formation with an enantiomer-pure chiral acid, or by means of chromatography, for example by HPLC, using chromatographic substrates with chiral ligands.

Routes of Administration

In therapeutic use for treating disorders in a mammal (i.e. human and animals), a compound of the present invention or its pharmaceutical compositions can be administered orally, parenterally, topically, rectally, transmucosally, or intestinally. Parenteral administrations include indirect injections to generate a systemic effect or direct injections to the afflicted area. Topical administrations include the treatment of skin or organs readily accessibly by local application, for example, eyes or ears. It also includes transdermal delivery to generate a systemic effect. The rectal administration includes the form of suppositories. The preferred routes of administration are oral and parenteral.

Pharmaceutical Salts

The compound of formula I may be used in its native form or as a salt. In cases where forming a stable nontoxic acid or base salt is desired, administration of the compound as a pharmaceutically acceptable salt may be appropriate. Pharmaceutically acceptable salts of the compounds of formula I include the acetate, ascorbate, aspartate, benzoate, besylate, bicarbonate/carbonate, bisulphate/sulphate, borate, camsylate, citrate, edisylate, etoglutarate, esylate, formate, fumarate, gluceptate, gluconate, glucuronate, glycerophosphate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Composition/Formulation

Pharmaceutical compositions of the present invention may be manufactured by processes well known in the art, e.g., by means of conventional mixing, dissolving, granulation, dragee-making, levigating, emulsifying, encapsulating, entrapping, lyophilizing processes or spray drying.

Pharmaceutical compositions for use in accordance with the present invention may be formulated in conventional manner using one or more pharmaceutically acceptable carriers comprising excipients and auxiliaries, which facilitate processing of the active compound into preparations, which can be used pharmaceutically. Proper formulation is dependent upon the route of administration chosen. Pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991).

The formulations of the invention can be designed to be short-acting, fast-releasing, long-acting, and sustained-releasing. Thus, the pharmaceutical formulations can also be formulated for controlled release or for slow release.

Dosage

Pharmaceutical compositions suitable for use in the present invention include compositions wherein the active ingredients are contained in an amount sufficient to achieve the intended purpose, i.e., control or the treatment of disorders or diseases. More specifically, a therapeutically effective amount means an amount of compound effective to prevent, alleviate or ameliorate symptoms/signs of disease or prolong the survival of the subject being treated.

The quantity of active component, which is the compound of this invention, in the pharmaceutical composition and unit dosage form thereof, may be varied or adjusted widely depending upon the manner of administration, the potency of the particular compound and the desired concentration. Determination of a therapeutically effective amount is well within the capability of those skilled in the art. Generally, the quantity of active component will range between 0.01% to 99% by weight of the composition.

Generally, a therapeutically effective amount of dosage of active component will be in the range of about 0.01 to about 100 mg/kg of body weight/day, preferably about 0.1 to about 10 mg/kg of body weight/day, more preferably about 0.3 to 3 mg/kg of body weight/day, even more preferably about 0.3 to 1.5 mg/kg of body weight/day It is to be understood that the dosages may vary depending upon the requirements of each subject and the severity of the disorders or diseases being treated.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Also, it is to be understood that the initial dosage administered may be increased beyond the above upper level in order to rapidly achieve the desired plasma concentration. On the other hand, the initial dosage may be smaller than the optimum and the daily dosage may be progressively increased during the course of treatment depending on the particular situation. If desired, the daily dose may also be divided into multiple doses for administration, e.g., two to four times per day.

Medical and Veterinary Uses

Compounds of the present invention are Janus Kinase inhibitors (JAK-i) with efficacy against Janus Kinase-1 (JAK-1), Janus Kinase-2 (JAK-2) and Janus Kinase-3 (JAK-3). Accordingly, they are useful as therapeutic agents for organ transplants, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, leukemia, osteoarthritis, control of pruritus, chronic respiratory disease and other indications where immunosuppression/immunomodulation would be desirable.

In addition, there are substantial needs for safe and efficacious agents to control atopic dermatitis in animals. The market for treating atopic dermatitis in animals is currently dominated by corticosteroids, which cause distressing and undesirable side effects in animals, specifically in companion animals such as dogs. Antihistamines are also used, but are poorly effective. A canine formulation of cyclosporine (ATOPICA™) is currently being marketed for atopic dermatitis, but is expensive and has a slow onset of efficacy. In addition, there are GI toleration issues with ATOPICA™. Compounds of present invention are JAK inhibitors with efficacy against JAK-1 and JAK-3. These compounds will be an alternative to steroid usage and provide resolution of chronic pruritus and inflammation that would either persist in atopic dermatitis or slowly regress following removal of allergen or causative agent, such as fleas in flea-allergic dermatitis.

Compounds of the present invention may be administered in a pharmaceutically acceptable form either alone or in combination with one or more additional agents which modulate a mammalian immune system or with antiinflammatory agents. These agents may include but are not limited to cyclosporin A (e.g. Sandimmune® or Neoral®, rapamycin, FK-506 (tacrolimus), leflunomide, deoxyspergualin, mycophenolate (e.g. Cellcept®, azathioprine (e.g. Imuran®), daclizumab (e.g. Zenapax®), OKT3 (e.g. Orthocolone®), AtGam, aspirin, acetaminophen, ibuprofen, naproxen, piroxicam, and antiinflammatory steroids (e.g. prednisolone or dexamethasone). These agents may be administered as part of the same or separate dosage forms, via the same or different routes of administration, and on the same or different administration schedules according to standard pharmaceutical practice known to one skilled in the art.

In one embodiment, the invention provides methods of treating or preventing a disease, condition or disorder associated with JAK in a subject, such as a human or non-human mammal, comprising administering an effective amount of one or more compounds described herein to the subject. The JAK associated disease, condition or disorder can be related to JAK-1, JAK-2, JAK-3, and/or Tyk-2. Suitable subjects that can be treated include domestic or wild animals, companion animals, such as dogs, cats, horses and the like; livestock including, cows and other ruminants, pigs, poultry, rabbits and the like; primates, for example monkeys, such as rhesus monkeys and cynomolgus (also known as crab-eating or long-tailed) monkeys, marmosets, tamarins, chimpanzees, macaques and the like; and rodents, such as rats, mice, gerbils, guinea pigs and the like. In one embodiment, the compound is administered in a pharmaceutically acceptable form, optionally in a pharmaceutically acceptable carrier.

JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas. For a review of the pharmaceutical intervention of the JAK/STAT pathway see Frank, (1999), Mol. Med. 5:432:456 and Seidel et al., (2000), Oncogene 19:2645-2656.

JAK-3 in particular has been implicated in a variety of biological processes. For example, the proliferation and survival of murine mast cells induced by IL-4 and IL-9 have been shown to be dependent on JAK-3 and gamma chain-signaling. Suzuki et al., (2000), Blood 96:2172-2180. JAK-3 also plays a crucial role in IgE receptor-mediated mast cell degranulation responses (Malaviya et al., (1999), Biochem. Biophys. Res. Commun 257:807-813), and inhibition of JAK-3 kinase has been shown to prevent type I hypersensitivity reactions, including anaphylaxis (Malaviya et al., (1999), J. Biol. Chem. 274:27028-27038). JAK-3 inhibition has also been shown to result in immune suppression for allograft rejection (Kirken, (2001), Transpl. Proc. 33:3268-3270). JAK-3 kinases have also been implicated in the mechanism involved in early and late stages of rheumatoid arthritis (Muller-Ladner et al., (2000), J. Immunal. 164:3894-3901); familial amyotrophic lateral sclerosis (Trieu et al., (2000), Biochem Biophys. Res. Commun. 267:22-25); leukemia (Sudbeck et al., (1999), Clin. Cancer Res. 5:1569-1582); mycosis fungoides, a form of T-cell lymphoma (Nielsen et al., (1997), Prac. Natl. Acad. Sci. USA 94:6764-6769); and abnormal cell growth (Yu et al., (1997), J. Immunol 159: 5206-5210; Catlett-Falcone et al., (1999), Immunity 10:105-115).

The JAK kinases, including JAK-3, are abundantly expressed in primary leukemic cells from children with acute lymphoblastic leukemia, the most common form of childhood cancer, and studies have correlated STAT activation in certain cells with signals regulating apoptosis (Demoulin et al., (1996), Mol. Cell. Biol. 16:4710-6; Jurlander et al., (1997), Blood 89:4146-52; Kaneko et al., (1997), Clin. Exp. Immun 109:185-193; and Nakamura et al., (1996), J. Biol. Chem. 271: 19483-8). They are also known to be important to lymphocyte differentiation, function and survival. JAK-3 in particular plays an essential role in the function of lymphocytes, macrophages, and mast cells. Given the importance of this JAK kinase, compounds which modulate the JAK pathway, including those selective for JAK-3, can be useful for treating diseases or conditions where the function of lymphocytes, macrophages, or mast cells is involved (Kudlacz et al., (2004) Am. J. Transplant 4:51-57; Changelian (2003) Science 302:875-878).

Conditions in which targeting of the JAK pathway or modulation of the JAK kinases, particularly JAK-3, are contemplated to be therapeutically useful include, arthritis, asthma, autoimmune diseases, cancers or tumors, diabetes, certain eye diseases, disorders or conditions, inflammation, intestinal inflammations, allergies or conditions, neurodegenerative diseases, psoriasis, transplant rejection, and viral infection. Conditions which can benefit for inhibition of JAK-3 are discussed in greater detail below.

Accordingly, the compound of formula I or its pharmaceutically acceptable salts and pharmaceutical compositions can be used to treat a variety of conditions or diseases such as:

Arthritis, including rheumatoid arthritis, juvenile arthritis, and psoriatic arthritis;

Asthma and other obstructive airways diseases, including chronic or inveterate asthma, late asthma, airway hyper-responsiveness, bronchitis, bronchial asthma, allergic asthma, intrinsic asthma, extrinsic asthma, dust asthma, recurrent airway obstruction, and chronic obstruction pulmonary disease;

Autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be O-cell (humoral) based or T-cell based, including Cogan's syndrome, ankylosing spondylitis, Wegener's granulomatosis, autoimmune alopecia, Type I or juvenile onset diabetes, and thyroiditis;

Cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma, leukemia, including acute myelogenous leukemia and chronic myelogenous leukemia, kidney cancer, lung cancer, muscle cancer, bone cancer, bladder cancer, brain cancer, melanoma including oral and metastatic melanoma, Kaposi's sarcoma, myelomas including multiple myeloma, myeloproliferative disorders, proliferative diabetic retinopathy, and angiogenic-associated disorders including solid tumors;

Diabetes, including Type I diabetes and complications from diabetes;

Eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization;

Intestinal inflammations, allergies or conditions including Crohn's disease and/or ulcerative colitis, inflammatory bowel disease, coeliac diseases, proctitis, eosinophilic gastroenteritis, and mastocytosis;

Neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia, and platelet aggregation;

Skin diseases, conditions or disorders including atopic dermatitis, eczema, psoriasis, scleroderma, pruritus and other pruritic conditions;

Allergic reactions including allergic dermatitis in mammal including horse allergic diseases such as bite hypersensitivity, summer eczema and sweet itch in horses.

Transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation; and Another embodiment provides a method of inhibiting a JAK enzyme, including JAK-1, JAK-2, JAK-3 and/or Tyk-2, that includes contacting the JAK enzyme with either a non-therapeutic amount or a therapeutically effective amount of one or more of the present compounds. Such methods can occur in vivo or in vitro. In vitro contact can involve a screening assay to determine the efficacy of the one or more compounds against a selected enzyme at various amounts or concentrations. In vivo contact with a therapeutically effective amount of the one or more compounds can involve treatment of a described disease, disorder or condition or prophylaxis of organ transplant rejection in the animal in which the contact occurs. The effect of the one or more compounds on the JAK enzyme and/or host animal can also be determined or measured. Methods for determining JAK activity include those described in the Examples as well as those disclosed in WO 99/65908, WO 99/65909, WO 01/42246, WO 02/00661, WO 02/096909, WO 2004/046112 or WO 2007/012953.

The following reaction schemes illustrate the general synthetic procedures of the compounds of the present invention. All starting materials are prepared by procedures described in these schemes or by procedures known to one of ordinary skill in the art.

It will be apparent to those skilled in the art that sensitive functional groups (Pg or Pg1) may need to be protected and deprotected during synthesis of a compound of the invention. This may be achieved by conventional methods, for example as described in "Protective Groups in Organic Synthesis" by TW Greene and PGM Wuts, John Wiley & Sons Inc (1999), and references therein.

In Scheme I, 4-Chloro-7H-pyrrolo[2,3-d]pyrimidine (a) can be obtained commercially. trans-4-(Methylamino)-cyclohexyl]methanol (b) may be obtained from the corresponding carboxylic acid, trans-4-[(tert-butoxycarbonyl)amino]cyclohexanecarboxylic acid, upon treatment with a reducing agent such as lithium aluminium hydride in an aprotic, anhy-

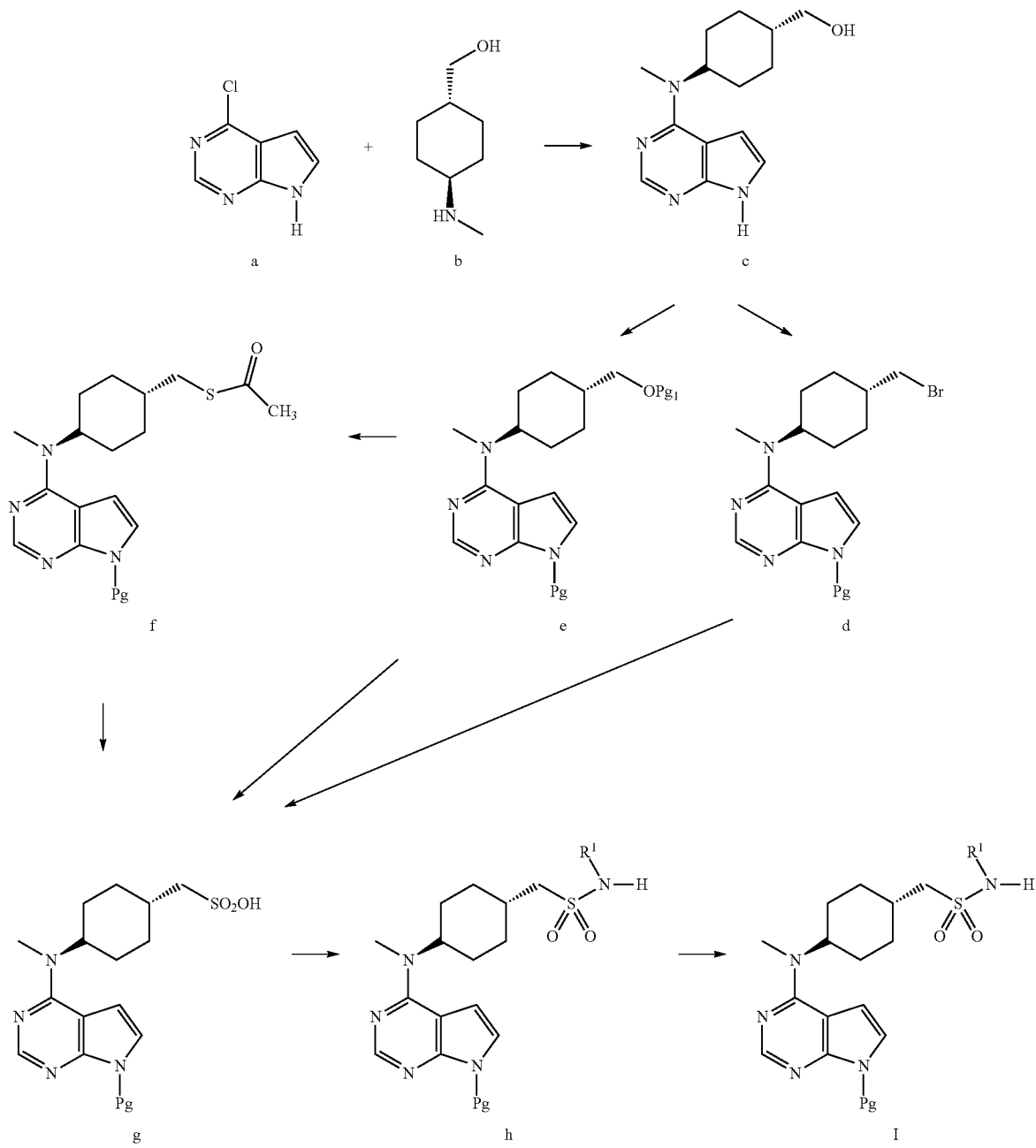

drous solvent such as tetrahydrofuran at temperatures between 0-60° C. for several hours.

As shown in Scheme I, a compound of structure (c) can be synthesized by the reaction of 4-chloro-7H-pyrrolo[2,3-d]pyrimidine (a) with trans-4-(methylamino)-cyclohexyl] methanol (b) in a suitable aprotic, polar solvent such as N,N-dimethylformamide, aqueous dioxane and dimethylsulfoxide, in the presence of a suitable base such as triethylamine and potassium carbonate at elevated temperatures up to 90° C. for up to a few hours.

A compound of structure (d) could be synthesized in a two step procedure from a compound of structure (c). For example, a compound of structure (d) would be synthesized by firstly using brominating reagents such as thionyl bromide or phosphorous tribromide in a polar, aprotic solvent such as methylene chloride to afford the unprotected cyclohexylmethylbromide, and secondly by addition of a suitable protecting reagent such as tosyl chloride to give the protected compound of structure (d).

A compound of structure (e) can be prepared by using simple protection processes from a compound of structure (c). For example, when Pg and Pg$_1$ are both tosyl, this can be effected in a one step reaction upon treatment of the unprotected compound of structure (c) with tosyl chloride in the presence of a polar, aprotic solvent such as methylene chloride, a catalyst such as DMAP and a weak base such as triethylamine.

A compound of structure (f) may be synthesized from a compound of structure (e) by S-alkylation using a suitable nucleophile. Thus compounds of structure (e) wherein the protecting group (PO is a suitable hydroxyl protecting group such as tosyl or mesyl may be reacted with potassium thioacetate in a polar solvent such as dimethylsulfoxide or N-methylpyrrolidine at elevated temperatures up to 75° C. for up to 2 hours to give compounds of structure (f).

A compound of structure (g) may be synthesized by an oxidation procedure from compounds of formula (f). Many oxidizing conditions are known to those skilled in the art, for example those described in "Handbook of Reagents for Organic Synthesis—Oxidising and Reducing Agents" edited by S. D. Burke and R. L. Danheiser. For example, a compound of structure (f), optionally wetted with water, can be treated with formic acid followed by slow addition of hydrogen peroxide whilst stirring at room temperature for about 15 hours to give a compound of structure (g). Alternatively, oxone may be employed in a polar solvent such as acetic acid, if the reaction is performed in the presence of potassium acetate the potassium salt of the compound of formula (g) is produced.

It is envisaged that a compound of structure (g) may be synthesized directly from a compound of structure (e) upon treatment with a suitable sulfur nucleophile such as sodium sulfite in a polar solvent. Similarly, a compound of structure (g) could be synthesized from a compound of structure (d) upon nucleophilic substitution with sodium sulfite.

Treatment of sulphonic acids of formula (g) with a chlorinating agent such as thionyl chloride in an aprotic, polar solvent such as methylene chloride with a polar cosolvent such as N,N-dimethylformamide at reflux gives the chlorinated compounds. The chlorinated compound then reacts in an aprotic, anhydrous solvent such as tetrahydrofuran with suitable amines in neat, gaseous form, or dissolved in an aprotic, anhydrous solvents such as tetrahydrofuran, at room temperature to produce a compound of structure (h). Optionally an anhydrous, weak base such as triethylamine may be used to mop up hydrochloric acid generated in the reaction.

Compounds of formula I of the present invention may be prepared from compounds of formula (h) wherein Pg is a suitable protecting group by deprotection procedures known to one skilled in the art. For example, when the protecting group (Pg) is tosyl, suitable deprotection conditions involve reaction with a base such as lithium hydroxide or potassium hydroxide in a protic solvent such as methanol or isopropanol and optionally miscible cosolvents such as tetrahydrofuran and water at room temperature for several hours, to produce the deprotected amine of formula I.

Salts of compounds of formula I may be formed by the reaction of the free base of compounds of formula I with a suitable acid such as maleic acid in the presence of a protic solvent such as butanol and optionally a cosolvent such as water.

Alternatively, compounds of this invention can be prepared in accordance with Scheme II.

Scheme II

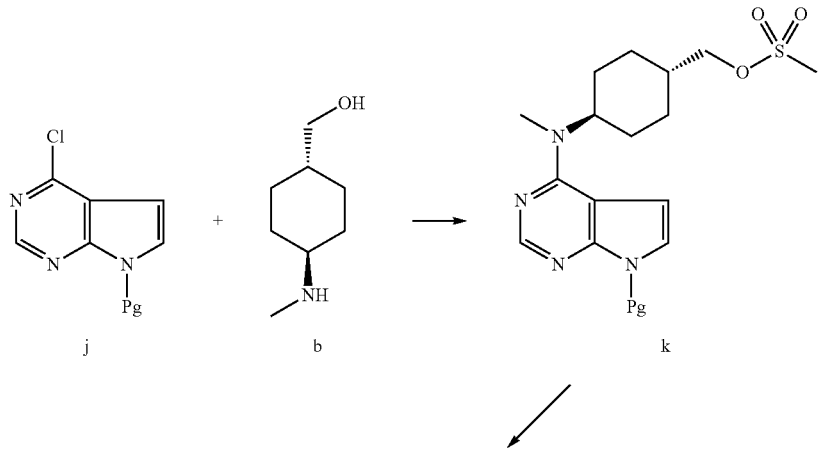

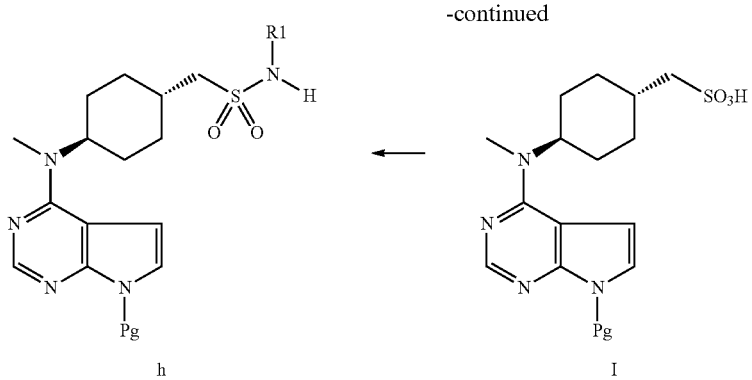

-continued

In Scheme II, 4-methyl-7-[(4-methylphenyl)sulfonyl]-7H-pyrrolo[2,3-d]pyrimidine (j) can be obtained from commercially available (a) using a protecting agent such as tosyl chloride using procedures well known in the art. trans-4-(Methylamino)-cyclohexyl]methanol (b) may be obtained from the corresponding carboxylic acid, trans-4-[(tert-butoxycarbonyl)amino]cyclohexanecarboxylic acid, upon treatment with a reducing agent such as Vitride in an anhydrous solvent such as toluene at temperatures between 0-110° C. for several hours.

As shown in Scheme II, a compound of structure (k) can be synthesized by the reaction of 4-chloro-7H-pyrrolo[2,3-d] pyrimidine (j) with trans-4-(methylamino)-cyclohexyl] methanol (b) in a suitable solvent such as acetone, in the presence of a suitable base such as triethylamine with a catalytic amount of potassium iodide at elevated temperatures up to 60° C. for up to a few hours.

A compound of structure (k) could synthesized by addition of a suitable mesylating reagent such as mesyl chloride in the presence of a suitable base such as triethylamine or diethylisopropylamine in a suitable solvent such as acetone at elevated temperatures up to 60° C. to give the methane sulfonyl compound of structure (k).

A compound of structure (l) can be prepared by using simple S-alkylation processes from a compound of structure (k) using a suitable nucleophile. Thus compounds of structure (k) may be reacted with sodium sulphite in solvent such as isopropylalcohol or water or toluene at elevated temperatures up to 90° C. for up to 4 hours to give compounds of structure (l).

Treatment of sulphonic acids of formula (l) with a chlorinating agent such as thionyl chloride in an aprotic, polar solvent such as THF or methylene chloride with a polar cosolvent such as N,N-dimethylformamide at temperatures between 0 and 40° C. gives the chlorinated compounds. The chlorinated compound then reacts in an aprotic, anhydrous solvent such as tetrahydrofuran with suitable amines such as methyl amine, cyclobutyl amine or 2-hydroxyazetidine preferably in neat, gaseous form, or dissolved in an aprotic, anhydrous solvents such as tetrahydrofuran, at room temperature to produce a compound of structure (h). Optionally an anhydrous, weak base such as triethylamine may be used to mop up hydrochloric acid generated in the reaction.

EXAMPLES

Preparation 1

N-Methyl-1-[trans-4-(methyl{7-[(4-methylphenyl) sulfonyl]-7H-pyrrolo[2,3-d]pyrimidin-4-yl}amino) cyclohexyl]methanesulfonamide

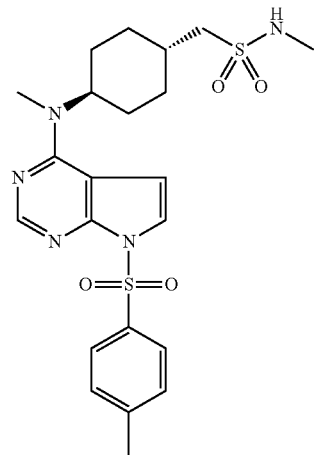 [SMILES: CNS(=O)(=O)C[C@H]1CC[C@H](N(C)c2ncnc3c2ccn3S(=O)(=O)c2ccc(C)cc2)CC1]

Method (a) To a solution of the compound of Preparation 2 (308.0 g wet weight, 214.5 g dry weight, 0.41 mol) in tetrahydrofuran (1.0 l) is added methylamine (2M in tetrahydrofuran, 687 ml) over 1 h. After stirring at room temperature for 30 min, additional methylamine (2M in tetrahydrofuran, 53 ml) is added and the reaction mixture is stirred at room temperature for 18 h. The mixture is reduced in volume to 600 ml, via vacuum distillation, and tetrahydrofuran (300 ml) is added, before the mixture is again reduced in volume to approximately 750 ml. To the mixture, heated at 45° C., is added 2-propanol (247 ml) and water (693 ml). After cooling to room temperature, the solid material is collected by filtration, washed with water (2×250 ml) and dried in vacuo at 65° C. to give the title compound (180.4 g).

$^1$H-NMR (d$_6$-DMSO): 1.17-1.32 (2H), 1.57-1.73 (4H), 1.76-1.92 (1H), 1.93-2.08 (2H), 2.30-2.39 (3H), 2.53-2.62

(3H), 2.87-2.98 (2H), 3.07-3.17 (3H), 4.53-4.75 (1H), 6.81-6.94 (1H), 7.38-7.47 (2H), 7.56-7.65 (1H), 7.92-8.02 (2H), 8.15-8.27 (1H).

Method (b) To a solution of the compound of Preparation 2 (165 g, 0.34 mol) in THF (1.65 l) and N,N-dimethylformamide (5.0 ml) at 0-5° C. is added thionyl chloride (125 ml, 17 mol), over 25 min. The reaction mixture was stirred for 30 minutes at 0-5° C. then slowly heated to 40° C. for 8 h. After cooling to r.t. the solvent was evaporated under reduced pressure and azeotroped with THF to removed thionyl chloride. To the sulphonyl chloride obtained was added fresh THF (1.65 l) and the mixture cooled to 0° C. Dry N-methylamine gas was purged for 30 minutes and the reaction stirred for a further 4 hours at r.t. The solvent was evaporated to half of its volume (800 ml) and heptane (1.5 l) added. The product precipitated out and was filtered and washed with water (1 l) to give the title compound (80 g).

$^1$H-NMR (d$_6$-DMSO): 1.17-1.32 (2H), 1.57-1.73 (4H), 1.76-1.92 (1H), 1.93-2.08 (2H), 2.30-2.39 (3H), 2.53-2.62 (3H), 2.87-2.98 (2H), 3.07-3.17 (3H), 4.53-4.75 (1H), 6.81-6.94 (1H), 7.38-7.47 (2H), 7.56-7.65 (1H), 7.92-8.02 (2H), 8.15-8.27 (1H)

Preparation 2

[trans-4-(Methyl{7-[(4-methylphenyl)sulfonyl]-7H-pyrrolo[2,3-d]pyrimidin-4-yl}amino)cyclohexyl]methanesulfonyl chloride

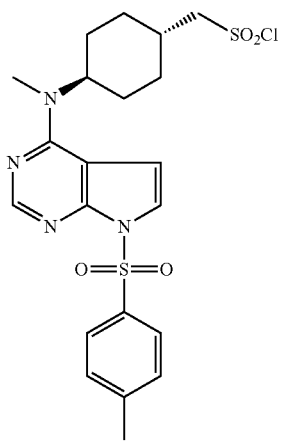 [SMILES: Cc1ccc(S(=O)(=O)n2ccc3c(N(C)[C@H]4CC[C@H](CS(=O)(=O)Cl)CC4)ncnc32)cc1]

To a solution of the compound of Preparation 3 (210.0 g, 0.42 mol) in dichloromethane (1.2 l) and N,N-dimethylformamide (4.1 ml) is added thionyl chloride (151.0 ml, 2.1 mol), over 25 min. The reaction mixture is heated at reflux for 18 h and then reduced in volume to 800 ml, via vacuum distillation. To the mixture, heated at approximately 30° C., is added ethyl acetate (1.1 l) over 1 h, followed by heptane (546 ml), added over 20 min at room temperature. The mixture is cooled to 0° C. and stirred for 1 h and the resulting precipitate is collected by filtration under nitrogen. The solid is washed with heptane (2×125 ml) to give the title compound (308.0 g wet weight), which is stored under nitrogen and used directly.

Preparation 3

[trans-4-(Methyl{7-[(4-methylphenyl)sulfonyl]-7H-pyrrolo[2,3-d]pyrimidin-4-yl}amino)cyclohexyl]methanesulfonic acid

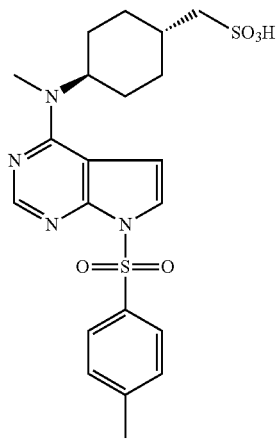 [SMILES: Cc1ccc(S(=O)(=O)n2ccc3c(N(C)[C@H]4CC[C@H](CS(=O)(=O)O)CC4)ncnc32)cc1]

Method (a) To a mixture of the compound of Preparation 4 (100.0 g wet weight, 23.5 g dry weight, 47.8 mmol) and formic acid (82.0 g, 68.0 ml, 1.8 mol) is added hydrogen peroxide (35 wt. % in water, 21.0 ml, 0.26 mol) over 10 min. The reaction mixture is stirred at room temperature for 15 h and then quenched by addition to an aqueous sodium metabisulfate or metabisulfite solution (33 wt. %, 35 ml). To the mixture is added water (5 ml), 2-propanol (50 ml) and aqueous sodium hydroxide solution (33 wt. %, 161 ml) and the slurry is stirred at room temperature for 1 h. The solid material is collected by filtration, washed with water (100 ml) and dried in vacuo at 60° C. to give the title compound (26.0 g).

$^1$H-NMR (d$_6$-DMSO): 0.98-1.18 (2H), 1.55-1.76 (5H), 1.99-2.13 (2H), 2.29-2.39 (5H), 3.05-3.15 (3H), 4.47-4.76 (1H), 6.77-6.92 (1H), 7.38-7.48 (2H), 7.54-7.62 (1H), 7.91-8.02 (2H), 8.17-8.25 (1H)

Method (b) To a solution of the compound of Preparation 3 in IPA-water (585 ml each, 1:1, V/V) was added sodium sulphate and the mixture was heated to 80-90° C. for 24 hours. After allowing to cool to r.t. the solvent was evaporated up to 50% and the pH of the reaction mixture adjusted in the range 3-4 by addition of acetic acid. Toluene (1 l) was added and the mixture evaporated to 80%. Further toluene (1 l) was added and the mixture refluxed for 4 hours. The toluene was decanted and the resultant title compound obtained by drying under vacuum (168 g).

$^1$H-NMR (d$_6$-DMSO): 0.98-1.18 (2H), 1.55-1.76 (5H), 1.99-2.13 (2H), 2.29-2.39 (5H), 3.05-3.15 (3H), 4.47-4.76 (1H), 6.77-6.92 (1H), 7.38-7.48 (2H), 7.54-7.62 (1H), 7.91-8.02 (2H), 8.17-8.25 (1H)

Preparation 4

S-{[trans-4-(Methyl{7-[(4-methylphenyl)sulfonyl]-7H-pyrrolo[2,3-d]pyrimidin-4-yl}amino)cyclohexyl]methyl}ethanethioate

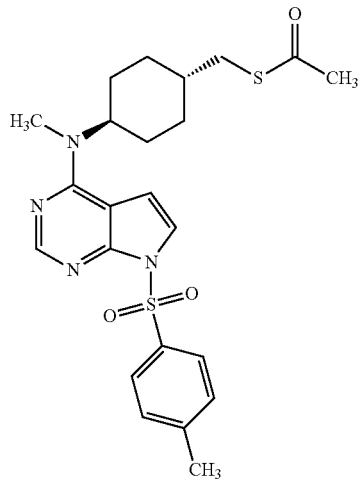 [SMILES: CC(=O)SC[C@H]1CC[C@H](N(C)c2ncnc3c2ccn3S(=O)(=O)c2ccc(C)cc2)CC1]

To a solution of potassium thioacetate (11.4 g, 99.4 mmol) in dimethyl sulfoxide (30 ml) is added the compound of Preparation 5 (50.0 g, 87.9 mmol) in dimethyl sulfoxide (130 ml). The reaction mixture is heated at 55° C. for 3 h, cooled to room temperature and quenched by addition to an aqueous sodium hydrogen carbonate solution (0.1M, 640 ml). The mixture is cooled to 13° C. and the resulting precipitate is collected by filtration and washed with water (250 ml) to give the title compound (204.0 g wet weight).

$^1$H-NMR (d$_6$-DMSO): 1.06-1.23 (2H), 1.39-1.51 (1H), 1.51-1.70 (4H), 1.74-1.88 (2H), 2.30-2.40 (6H), 2.73-2.84 (2H), 3.06-3.14 (3H), 4.44-4.76 (1H), 6.76-6.94 (1H), 7.36-7.49 (2H), 7.56-7.62 (1H), 7.90-8.02 (2H), 8.17-8.26 (1H)

Preparation 5

[trans-4-(Methyl{7-[(4-methylphenyl)sulfonyl]-7H-pyrrolo[2,3-d]pyrimidin-4-yl}amino)cyclohexyl]methyl 4-methylbenzenesulfonate

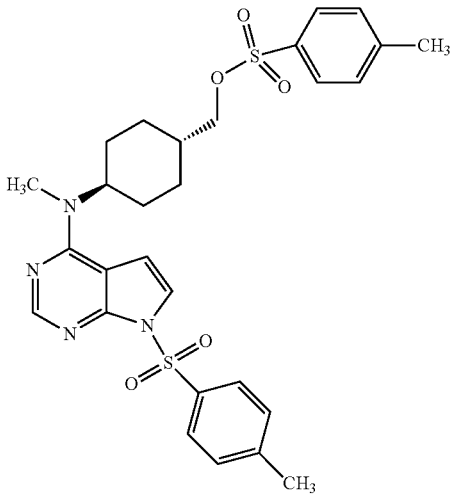 [SMILES: Cc1ccc(S(=O)(=O)OC[C@H]2CC[C@H](N(C)c3ncnc4c3ccn4S(=O)(=O)c3ccc(C)cc3)CC2)cc1]

To a solution of the compound of Preparation 6 (42.0 g, 0.16 mol) in dichloromethane (1 l) is added triethylamine (68.3 g, 0.68 mol) and 4-dimethylaminopyridine (1.0 g, 8.2 mmol), followed by p-toluenesulfonyl chloride (62 g, 0.33 mol). The reaction mixture is stirred at room temperature for 2 h, before addition of further p-toluenesulfonyl chloride (45.5 g, 0.24 mol). After stirring for 18 h, the mixture is concentrated in vacuo and a portion of the residue (approximately 309 g) is slurried in methanol (758 ml) for 15 min. To the slurry is added water (600 ml) and saturated aqueous sodium hydrogen carbonate solution (142 ml) and the mixture is stirred for 1 h. The solid material is collected by filtration and washed with methanol:water [1:1, 50 ml], water (50 ml) and hexanes (50 ml). The solid is dried in vacuo at 60° C. to give the title compound (87.1 g).

$^1$H-NMR (d$_6$-DMSO): 1.02-1.20 (2H), 1.53-1.75 (7H), 2.31-2.39 (3H), 2.39-2.47 (3H), 3.04-3.12 (3H), 3.80-3.91 (2H), 4.34-4.76 (1H), 6.78-6.93 (1H), 7.37-7.54 (4H), 7.54-7.64 (1H), 7.75-7.84 (2H), 7.91-8.01 (2H), 8.14-8.25 (1H)

Preparation 6

{trans-4-[Methyl(7H-pyrrolo[2,3-d]pyrimidin-4-yl)amino]cyclohexyl}-methanol

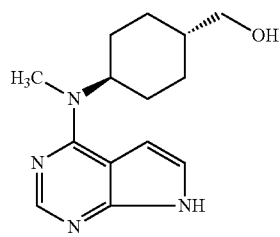 [SMILES: CN(c1ncnc2[nH]ccc12)[C@H]1CC[C@H](CO)CC1]

A mixture of the compound of trans-4-(Methylamino)cyclohexyl]methanol (may be prepared according to the procedure described in WO 2002/14267)(50.0 g, 0.35 mol), 4-chloro-7H-pyrrolo[2,3-d]pyrimidine (commercially available, 42.9 g, 0.27 mol) and potassium carbonate (57.3 g, 0.42 mol) in water (1 l) and 1,4-dioxane (100 ml) is heated at 90° C. for 15 h. To the mixture is added the compound of Preparation 7 (2.0 g, 14.0 mmol) and the reaction mixture is heated at 90° C. for a further 1 h. After cooling to room temperature, the mixture is stirred for 1 h and the solid material is collected by filtration, washed with water (150 ml) and dried in vacuo at 65° C. to give the title compound (72.7 g).

$^1$H-NMR (d$_6$-DMSO): 1.00-1.19 (2H), 1.30-1.45 (1H), 1.52-1.77 (4H), 1.77-1.91 (2H), 3.09-3.20 (3H), 3.20-3.29 (2H), 4.37-4.51 (1H), 6.45-6.57 (1H), 7.06-7.17 (1H), 8.01-8.14 (1H)

Preparation 7

[trans-4-(Methyl{7-[(4-methylphenyl)sulfonyl]-7H-pyrrolo[2,3-d]pyrimidin-4-yl}amino)cyclohexyl]methanesulfinate

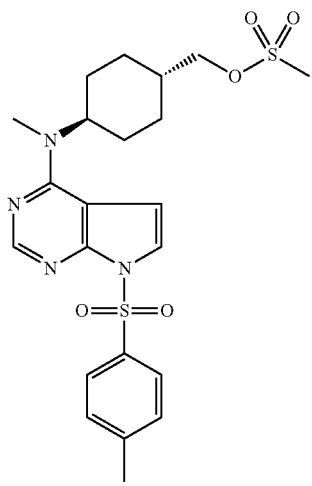 [SMILES: Cc1ccc(S(=O)(=O)n2ccc3c(N(C)[C@H]4CC[C@H](COS(C)(=O)=O)CC4)ncnc32)cc1]

To a solution of the compound of Preparation 4 (60.0 g, 0.418 mol) in acetone (600 ml) is added triethylamine (117.5 ml, 0.837 mol) and catalytic potassium iodide (3.4 g, 0.05 mol), followed by 4-chloro-7H-pyrrolo[2,3-d]pyrimidine (commercially available, 102.8 g, 0.335 mol). The resulting mixture was heated to 60° C. for 22 h. After allowing to cool to r.t. acetone (300 ml) was added, followed by triethylamine (146.9 ml, 1.04 mol) then mesyl chloride (81.7 ml, 1.047 mol). After stirring for 4 hours at r.t. water was added (1.8 l) whereupon the product precipitated out. The product was filtered, dried and triturated with a mixture of MTBE-heptane (6:4, 600 ml). A second trituration from MTBE-heptane was conducted and the resultant title compound obtained (120 g).

$^1$H-NMR (d$_6$-DMSO):

Preparation 8

[trans-4-(Methylamino)cyclohexyl]methanol

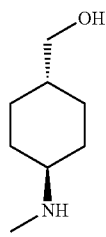

Vitride solution (65%, 767 ml, 2.465 mol) was added dropwise over 1 h to a solution of trans-4-[(tert-butoxycarbonyl)amino]cyclohexanecarboxylic acid (commercially available, 100 g, 0.4109 mol) in toluene (1 l). After the addition was complete the reaction mixture was heated to reflux for 100-110° C. The reaction mixture was quenched with aq. Sodium sulphate solution (800 ml) at temperatures below 10° C. The reaction mixture was filtered through celite and the filter cake washed with DCM (500 ml) followed by water (100 ml). The organics layer was separated and the aqueous layer extracted twice with DCM (600 ml then 400 ml). The combined organics layers were dried over sodium sulphate and concentrated in vacuo to give the title compound (62 g).

$^1$H-NMR (CD$_3$OD): 1.08-1.31 (4H), 1.51-1.64 (1H), 1.93-2.05 (2H), 2.10-2.22 (2H), 2.38-2.50 (1H), 2.50-2.54 (3H), 3.48-3.55 (2H)

Example 1a

Preparation of N-methyl-1-{trans-4-[methyl(7H-pyrrolo[2,3-d]pyrimidin-4-yl)amino]cyclohexyl}methanesulfonamide

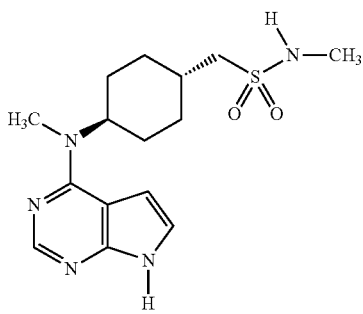 [SMILES: CNS(=O)(=O)C[C@H]1CC[C@H](N(C)c2ncnc3[nH]ccc23)CC1]

To a solution of the compound of Preparation 1 (250.0 g, 0.48 mol) in 2-propanol (1.2 l) is added lithium hydroxide (48.7 g, 2.03 mol) in water (1.2 l). The reaction mixture is heated at 40° C. for 8 h and then stirred at room temperature for 18 h. The mixture is filtered, washing through with 2-propanol:water (1:1, 100 ml) and the filtrate is adjusted to pH 7.5 by addition of hydrochloric acid (6N). After stirring for 1 h, the solid material is collected by filtration, washed with 2-propanol:water (1:2, 240 ml) and dried in vacuo at 60° C. to give the title compound (148.7 g) as a free base (Example 1a).

$^1$H-NMR (d$_6$-DMSO): 1.20-1.39 (2H), 1.62-1.75 (4H), 1.77-1.91 (1H), 1.97-2.11 (2H), 2.54-2.63 (3H), 2.89-2.99 (2H), 3.10-3.21 (3H), 4.44-4.86 (1H), 6.43-6.61 (1H), 7.01-7.19 (1H), 7.94-8.16 (1H)

Example 1b

Preparation of N-methyl-1-{trans-4-[methyl(7H-pyrrolo[2,3-d]pyrimidin-4-yl)amino]cyclohexyl}methanesulfonamide maleic acid salt A mixture of the compound of Example 1a (212.0 g, 628.3 mmol) and maleic acid (67.2 g, 579.0 mmol) in 1-butanol (3200 ml) and water (400 ml) is stirred at room temperature for 18 h. The mixture is reduced in volume to 1600 ml, via vacuum distillation (55° C., 100 mbar) and then cooled to 0° C. The resulting solid is collected by filtration, washed with heptane (500 ml) and dried in vacuo at 35° C. to give the maleate salt of N-methyl-1-{trans-4-[methyl(7H-pyrrolo[2,3-d]pyrimidin-4-yl)amino]-cyclohexyl}methanesulfonamide (253.0 g) as a crystalline form known as Form A.

Experimental MH$^+$ 338.2; expected 338.2.

$^1$H-NMR (d$_6$-DMSO): 1.24-1.38 (2H), 1.68-1.92 (5H), 2.00-2.11 (2H), 2.56-2.61 (3H), 2.91-3.00 (2H), 3.15-3.27 (3H), 4.39-4.70 (1H), 6.53-6.73 (1H), 7.16-7.36 (1H), 8.07-8.29 (1H).

Example 1c

Method for collecting powder X-ray diffraction for N-methyl-1-{trans-4-[methyl(7H-pyrrolo[2,3-d]pyrimidin-4-yl)amino]cyclohexyl}-methanesulfonamide maleic acid salt (Form A)

The powder X-ray diffraction patterns for Form A, N-methyl-1-{trans-4-[methyl(7H-pyrrolo[2,3-d]pyrimidin-4-yl)amino]cyclohexyl}-methanesulfonamide maleic acid salt were collected using a Bruker-AXS Ltd. D4 powder X-ray diffractometer fitted with an automatic sample changer, a theta-theta goniometer, automatic beam divergence slit, and a PSD Vantec-1 detector. The sample was prepared for analysis by mounting on a low background cavity silicon wafer specimen mount. The specimen was rotated whilst being irradiated with copper K-alpha$_1$ X-rays (wavelength=1.5406 Angstroms) with the X-ray tube operated at 40 kV/35 mA. The analyses were performed with the goniometer running in continuous mode set for a 0.2 second count per 0.018° step over a two theta range of 2° to 55°. The results are summarized in Table 1 and Table 2.

TABLE 1

Powder X-ray Diffraction Peaks expressed in degrees 2-theta, ±0.2 degrees, approximately

| Angle 2-theta | Intensity I% |
|---|---|
| 6.178 | 72.6 |
| 8.519 | 24.5 |
| 12.601 | 88.4 |
| 13.819 | 38 |
| 15.478 | 34.3 |
| 15.719 | 100 |
| 16.32 | 27.1 |
| 17.997 | 32.3 |
| 18.539 | 44.5 |
| 20.298 | 18.2 |
| 20.659 | 27.8 |
| 21.583 | 11.1 |
| 22.642 | 12.7 |
| 23.08 | 12.1 |
| 24.86 | 19.8 |
| 25.602 | 10.7 |
| 26.582 | 13 |
| 27.02 | 30.6 |
| 27.721 | 18.7 |
| 28.161 | 23.7 |
| 28.38 | 28.9 |

TABLE 2

Selected Powder X-ray Diffraction Peaks expressed in degrees 2-theta, ±0.2 degrees, approximately

| Angle 2-theta | Lattice Dimension d(A) | Intensity I% |
|---|---|---|
| 6.179 | 14.3 | 73 |
| 12.601 | 7.01 | 88 |
| 15.719 | 5.63 | 100 |
| 18.539 | 4.78 | 45 |
| 27.02 | 3.29 | 30.6 |
| 28.38 | 3.14 | 28.9 |

As is readily apparent to one skilled in the art, the results of any X-ray powder diffraction may vary and subsequent XRPD's will not be identical, even when carried out on the same lot of material. This variance can be due to test sample preparation, temperature, the particular model of X-ray diffractometer used, the operator's technique, etc. The term "approximately" if used in defining a peak in an X-ray powder diffraction pattern is defined as the stated 2θ value±0.2°2θ. Any determination of whether a crystalline form is the Form A polymorph and encompassed by the claims should be interpreted in light of the variability in this test.

This variability is demonstrated in FIG. 1. The two different lots of N-methyl-1-{trans-4-[methyl(7H-pyrrolo[2,3-d]pyrimidin-4-yl)amino]cyclohexyl}-methanesulfonamide maleic acid salt Form A were submitted to the same XRPD diffractometer. The characteristic peaks in FIG. 1 confirming that it is the Form A polymorph. However, the relative intensity of these peaks as well as the other identifying peaks varied slightly.

Example 2

Preparation of N-cyclobutyl-1-{trans-4-[methyl(7H-pyrrolo[2,3-d]pyrimidin-4-yl)amino]cyclohexyl}methanesulfonamide

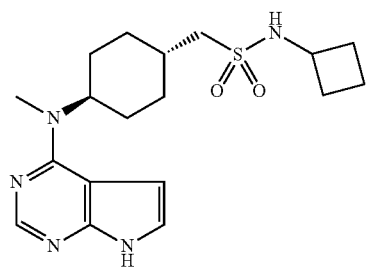 [SMILES: CN(c1ncnc2[nH]ccc12)[C@H]1CC[C@H](CS(=O)(=O)NC2CCC2)CC1]

Following the general procedure of Example 1 and making non-critical variations but substituting the precursor to cyclobutanamine, the title compound is provided. Experimental MH$^+$ 378.0; expected 378.2

$^1$H-NMR (d$_6$-DMSO): 1.22-1.32 (2H), 1.47-1.70 (6H), 1.78-2.04 (5H), 2.16-2.24 (2H), 2.85-2.86 (2H), 3.15 (3H). 3.68-3.78 (1H), 4.60-4.72 (1H), 6.51-6.54 (1H), 7.11-7.12 (1H), 7.44-7.49 (1H), 8.08 (1H), 11.60 (1H)

Example 3

Preparation of N-ethyl-1-{trans-4-[methyl(7H-pyrrolo[2,3-d]pyrimidin-4-yl)amino]cyclohexyl}methanesulfonamide

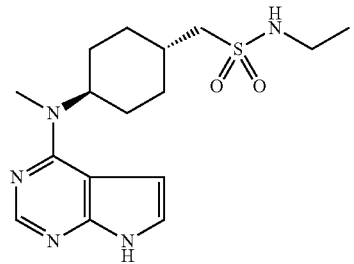 [SMILES: CCNS(=O)(=O)C[C@H]1CC[C@H](N(C)c2ncnc3[nH]ccc23)CC1]

Following the general procedure of Example 1 and making non-critical variations but substituting the precursor to ethanamine, the title compound is provided.

Experimental MH+ 352.0; expected 352.2

$^1$H-NMR (CDCl$_3$): 1.24-1.44 (5H), 1.64-1.74 (2H), 1.87-2.09 (3H), 2.15-2.21 (2H), 2.97-2.99 (2H), 3.18-3.27 (5H), 4.46-4.52 (1H), 4.74-4.86 (1H), 6.55 (1H), 7.04 (1H), 8.28 (1H)

Example 4

JAK Enzymatic Assay

Materials: Recombinant JAK-2 (Catalog Number PV4210) and JAK-3 (Catalog Number PV3855) were purchased from (Invitrogen Corporation, Madison, Wis.). Recombinant JAK-1 (GST-JAK-1 (852-1142)) and Tyk-2 (GST-Tyk2 (870-1187, C1187S)) used in this study were expressed and purified at Pfizer Laboratories. Adenosine 5'-triphosphate (ATP) was obtained from Sigma Chemical Company, St. Louis, Mo. The JAKtide peptide (peptide sequence, FITC-KGGEEEEYFELVKK (SEQ ID NO:1)) used for the JAK-2 and JAK-3 assays and the IRS-1 peptide (peptide sequence, 5-FAM-KKSRGDYMTMQIG (SEQ ID NO:2)) used for the JAK-1 and Tyk-2 assays were purchased from (American Peptide Company, Sunnyvale, Calif.). Coating Reagent 3 was purchased from (Caliper Life Sciences, Hopkinton, Mass.).

Methods: A peptide mobility shift assay was used to quantify the phosphorylation of the JAKtide (JAK-2 and JAK-3) or the IRS-1 peptide (JAK-1 and Tyk-2). Reactions were carried out in a 384-well plate (Matrical MP-101) in a 10 microliter total volume. Reaction mixtures contained 20 mM HEPES, pH 7.4, 10 mM magnesium chloride, 0.01% bovine serum albumin (BSA), 0.0005% Tween-20, ATP (4 micromolar for JAK-2 and JAK-3, 40 micromolar for JAK-1 and 7 micromolar for Tyk-2)), 2% DMSO and 1 micromolar peptide substrate (JAKtide for JAK-2 and JAK-3 or IRS-1 peptide for JAK-1 and Tyk-2). Compounds were diluted serially in 100% dimethyl sulfoxide and tested in an 11 point dose response in duplicate or quadruplicate (200 nl of compound/DMSO was added per 10 microliter reaction). The reactions were initiated by the addition of enzyme to the final concentration of 2 nM JAK-2, 1 nM JAK-3, 7 nM Tyk2 or 20 nM JAK-1. The assay was run for 240 minutes for JAK-1, 150 minutes for JAK-2, 90 minutes for JAK-3 and 60 minutes for Tyk-2. The assays were stopped at the specified times with 20 microliter of 140 mM HEPES, 22.5 mM EDTA and 0.15% Coating Reagent 3. The plates were placed on a LabChip 3000 (LC3000) instrument (Caliper Life Sciences) to measure the formation of phosphorylated peptide. Data was analyzed using Hits Well Analyzer Software from (Caliper Life Sciences) to obtain the amount of product formed.

Data was then imported into an internal application where each data point was expressed as % inhibition based on uninhibited and no enzyme controls. Dose-response data was then fit using a 4 parameter logistic equation (Equation 1) to determine an IC$_{50}$ value.

$$y = \frac{max - min}{1 + \left(\frac{x}{IC_{50}}\right)^s} + min \qquad \text{Equation 1}$$

Where max is the fitted uninhibited value, min is the fitted complete inhibition value, and s is the slope factor.

Using this protocol, the following results were generated for the title compounds of Example 1 and 2.

TABLE 3

JAK Enzymatic Assay Result

| Ex. # | JAK-1 IC$_{50}$ | JAK-2 IC$_{50}$ | JAK-3 IC$_{50}$ | Tyk-2 IC$_{50}$ |
|---|---|---|---|---|
| 1a | 9.53 nM | 17.5 nM | 95.1 nM | 75.1 nM |
| 2 | 45.0 nM | 101.0 nM | 742 nM | — |

Example 5

Canine In Vitro T-Cell Proliferation Assay

T-cell activation plays a key role in a variety of inflammatory and autoimmune disorders as well as asthma, allergies and pruritus. Since T-cell activation can, in part, can be triggered by cytokines that signal through the JAK-STAT pathway, a JAK inhibitor could be effective against such diseases involving aberrant T-cell activation.

Methods: Canine whole blood was collected in sodium heparin tubes from 29 beagle dogs and 23 mixed breed dogs. Whole blood (20 µL) was plated in 96-well plates (Costar 3598) with 180 µL of medium (RPMI 1640, Gibco #21870-076, with 1% heat inactivated fetal bovine serum, Gibco #10082-39, 292 µg/ml L-glutamine, Gibco #250030-081, 100 u/ml penicillin and 100 µg streptomycin per ml, Gibco #15140-122) containing vehicle control or test compound (0.001 to 10 µM), concanavalin A (ConA; 1 µg/ml, Sigma C5275), and canine interleukin-2 (IL-2; 50 ng/ml, R&D Systems 1815-CL/CF). Wells containing whole blood, medium with vehicle control and no ConA or IL-2 were used as background controls. Plates were incubated at 37° C. for 48 hours. Tritiated thymidine, 0.4 µCi/well (Perkin Elmer, Net027A-005MC), was added for 20 additional hours. Plates were frozen and then thawed, washed and filtered using a Brandel MLR-96 cell harvester and prewet filter mats (Wallac 1205-401, Perkin Elmer). Filters were dried at 60° C. for one hour (Precision 16EG convection oven) and placed into filter sample bags (Wallac 1205-411, Perkin Elmer) with 10 mL of scintillant (Wallac 1205-440, Perkin Elmer). Sealed filters were counted on a LKB Wallac 1205 Betaplate liquid scintillation counter. Data were collected via Gterm Betaplate program v1.1 (Wallac copyright 1989-1990) and transformed into percent inhibition, calculated using the following formula:

$$100 - \left[\frac{(\text{Mean Drug Treatment } cpm - \text{Mean } BCK\ cpm)}{(\text{Mean Non-Drug Treatment } cpm - \text{Mean } BCK\ cpm)} \times 100\right] = \% \text{ Inhibition}$$

Data were graphically displayed as percent inhibition using GraphPad Prism 4.0, and IC$_{50}$ curves were fitted using a point to point analysis.

Results The average IC$_{50}$ values obtained when using whole blood from beagles was 66.3 nM for the compound of Example 1a; 410 nM for Example 2; and 83 nM for Example 3. The average IC$_{50}$ value obtained when using whole blood from mixed breed dogs was 138 nM for the compound of Example 1a. These data suggest that the compounds of the present invention are effective in inhibiting T-cell proliferation, a key feature in many diseases.

Example 6

Reducing Flea-Associated Pruritus and Dermatitis Assay

Flea-associated pruritus and dermatitis are common skin conditions in dogs. Pruritus is one of the most severe clinical signs associated with flea associated dermatitis, and continued scratching, face rubbing, and foot chewing can lead to a variety of changes to the skin such as erythema, edema, alopecia, lichenification, and hyper pigmentation. Flea-associated pruritus and dermatitis can be induced experimentally. In these models, inflammatory cells and cytokines have been shown to mediate immune reactions to allergens. Therefore, a JAK inhibitor that inhibits signal transduction of pruritogenic and proinflammatory cytokine receptors could be effective in inhibiting, reducing or minimizing flea-associated pruritus and dermatitis.

Study Design

Twenty eight male and female dogs of mixed breeds ranging in weight from 5-35 kg and greater than one year of age were infested with approximately 100 unfed adult cat fleas (*Ctenocephalides felis*) 14 days prior to the start of dosing and reinfested with 30 fleas per dog every 4 days throughout the study. Seven days before dosing, twenty four dogs were randomized into three different treatment groups, placebo, 0.5 mg/kg or 0.25 mg/kg of the compound of Example 1b, based on visual analog scale (VAS) scores for skin lesions. Treatments were given orally twice a day for 28 days, and pruritic behavior as well as erythema and skin lesions were was assessed during the study. Pruritic behavior was recorded by placing dogs into pens with video recording capability, and recording their activity over 4 hours. Pruritic activity was quantitated by determining how many seconds the dogs spent scratching. Skin lesions were recorded by image capture of abdominal, inguinal region and the severity ranked according to a visual analog scale (VAS).

Statistical Analysis:

Video captured elapsed time of pruritic behavior was analyzed using a mixed linear model for repeated measures. The model included fixed effects of treatment and day of study and the interaction of treatment and day of study. Random effects included block, the interaction of block and treatment and error. Baseline data for pruritic behavior (day −1) were used as covariate in the analysis of pruritic behavior. Least squares means were used as estimates of treatment means. Standard errors of least squares means were estimated and 90% confidence intervals were constructed. Geometric means were computed from the least squares means for log-transformed data. A priori contrasts were used to assess treatment. Treatment differences were assessed at the 10% level of significance (P≤0.10).

Results

Figure 2:
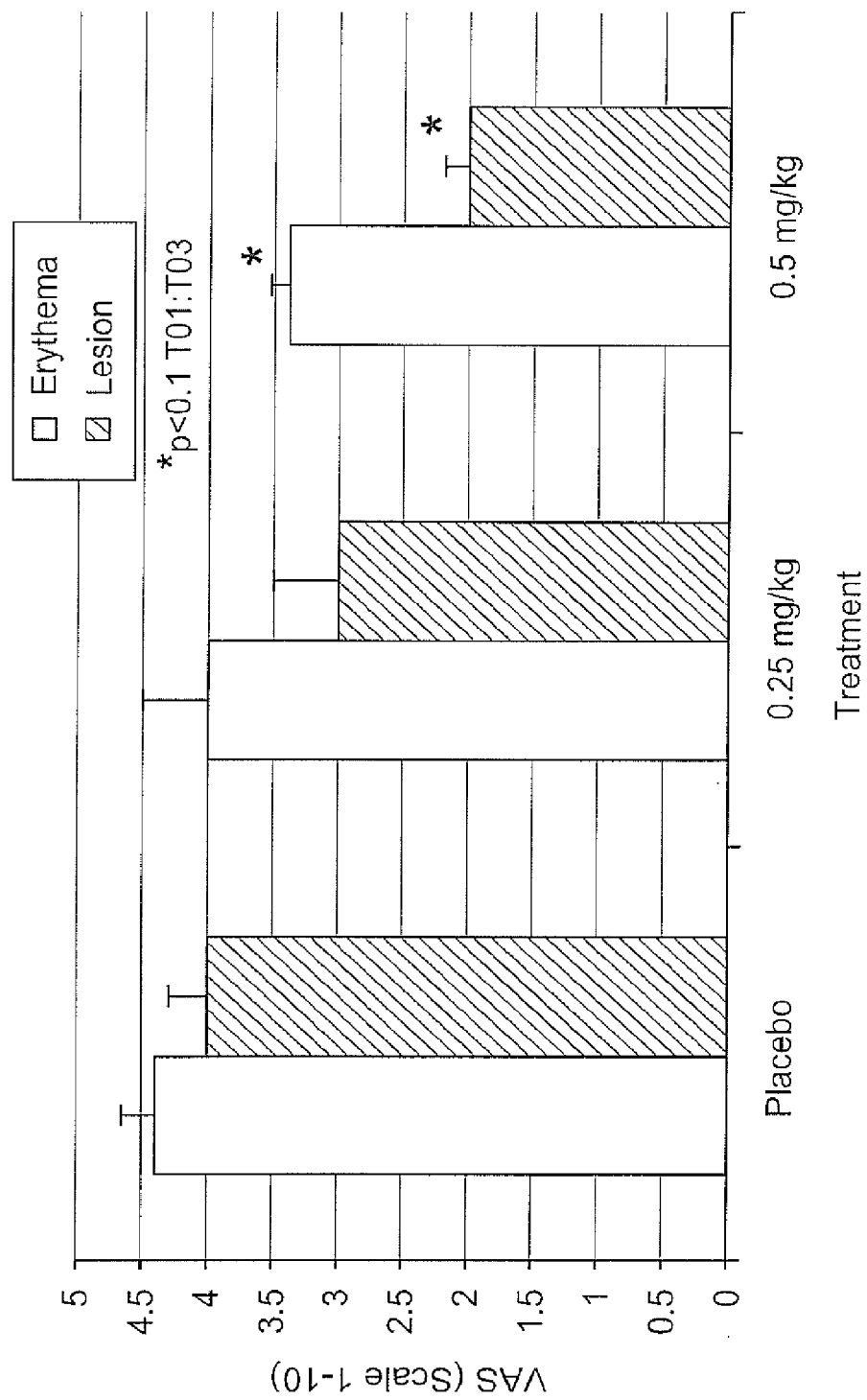
FIG. 2 illustrates Day 27 VAS Scores for Example 1b in flea allergic dogs in the Reducing Flea-associated Pruritus and Dermatitis Assay
Figure 3:
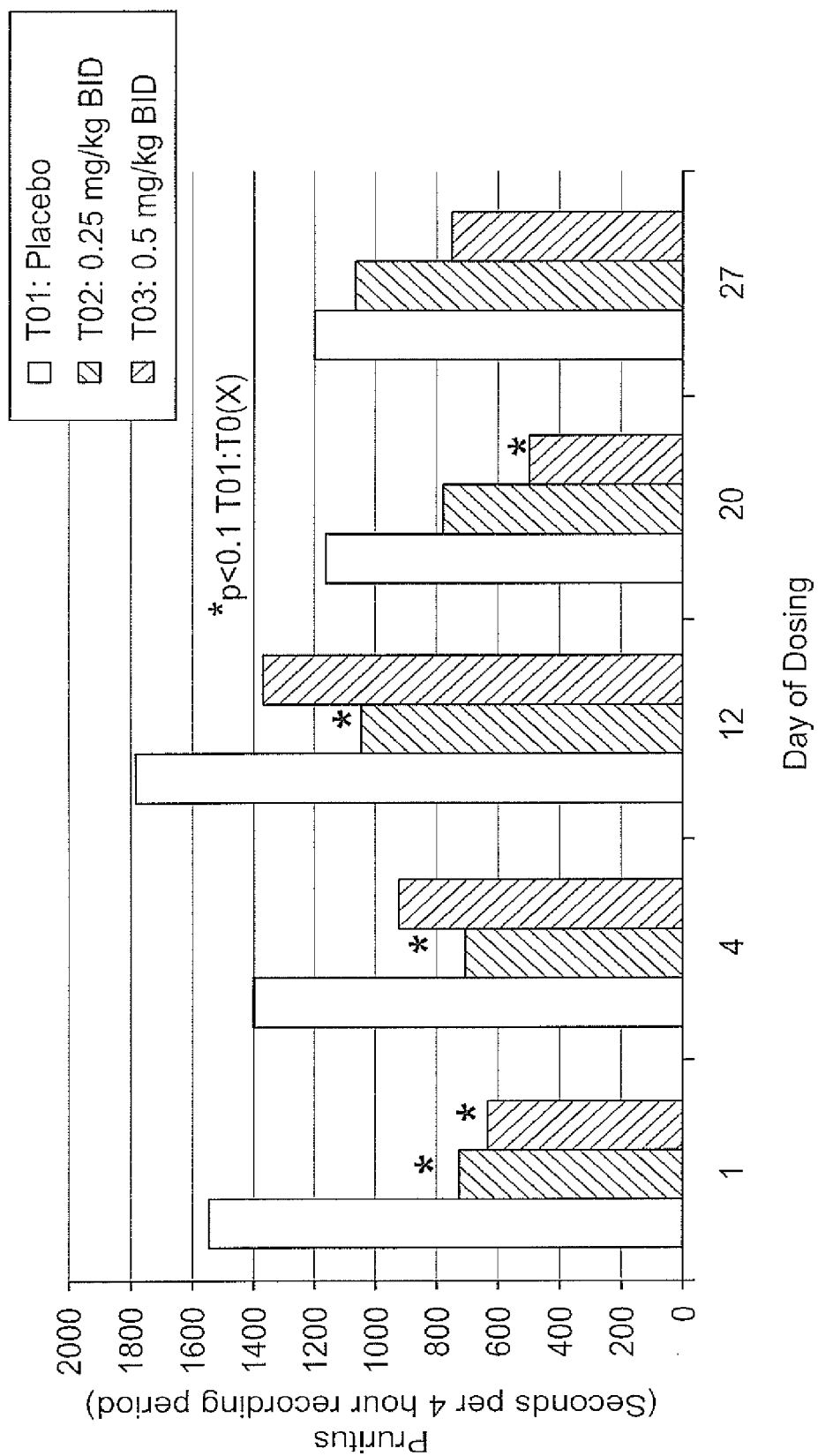
FIG. 3 illustrates Seconds of Pruritus per 4 hour recording for example 1b in flea allergic dogs in the Reducing Flea-associated Pruritus and Dermatitis Assay.

The treatment results are shown in FIG. 2 and FIG. 3. Lesions and erythema were significantly reduced in the 0.5 mg/kg group. FIG. 2 illustrates Day 27 VAS Scores for Example 1b in flea allergic dogs (Least Squares Means). Significant reductions in pruritus as compared to placebo at a 10% level of significance were seen at various time points during the study for both groups (days 1, 4 and 12 for the 0.25 mg/kg dose and on days 1 and 20 for the 0.5 mg/kg dose). FIG. 3 illustrates Seconds of Pruritus per 4 hour recording for example 1b in flea allergic dogs (Long Geometric Mean).

Example 7

Cell Proliferation Inhibitory Assay

Feline Cell Lines The MYA-1 and FETJ are feline T-lymphoblast cell lines obtained from ATCC (Manassas, Va.). These cells were cultured in RPMI 1640 complete media supplemented with 10% FBS at 37° C. in a humidified incubator with 5% $CO_2$.

Ex Vivo Canine Lymphoma Nodal Tissue

Malignant lymph nodes were excised by veterinary staff at Michigan State University (MSU) Veterinary College, placed into transport media (Advanced RPMI 1640 complete medium supplemented with 10% Fetal Bovine Serum (FBS), 100 U/mL penicillin, 100 ug/mL streptomycin and 0.25 ug/mL Amphotercin B (Invitrogen/Gibco®). Nodes were processed within 24 hours of removal by mincing into tiny pieces and passing through a tissue sieve. Cell suspensions were spun at 200×g, supernatant was removed, and the cell pellet was resuspended in $NH_4Cl$ for 10 minutes at room temperature. The cell suspension was pelleted by centrifugation; the $NH_4Cl$ was removed and washed once with Hanks Balanced Salt Solution (HBSS), followed by re-suspension in Proliferation Medium (Advanced RPMI complete, 1% FBS, 50 nM 2-Mercaptoethanol, 100 U/mL penicillin, 100 ug/mL streptomycin and 0.25 ug/mL Amphotericin B). The cell suspension was then passed through a 100 µm nylon cell strainer (BD-Falcon) and counted using a hemacytometer. Cells were cultured in either Proliferation Medium alone, Proliferation Medium supplemented with 0.005% Pansorbin® (Heat inactivated, formalin-fixed *Staphylococcus Aureus* cells (SAC), Calbiochem), and 10 ng/mL canine IL-2 (R&D Systems), or Proliferation Medium supplemented with 125 ng/mL concavalin A (Sigma) and 125 ng/mL lipopolysaccarride (LPS; Calbiochem).

In Vitro Anti-Proliferation Assay Method

Cells cultured in medium described above were plated in 96-well Costar plates (Corning) at a density of $1 \times 10^3$ cells/well (feline cell lines) or $2 \times 10^5$ cells/well (lymph node cells) and exposed to various concentrations of test compounds for up to 5 days at 37° C. in a humidified incubator with 5% $CO_2$. Effects on proliferation were determined using the CellTiter 96® $AQ_{ueous}$ Non-Radioactive Cell Proliferation Assay (Promega) according to manufacturer's instructions. In general, proliferation was indirectly measured using a soluble tetrazolium salt (MTS) and an electron coupling agent. MTS bioreduction into a formazan product soluble in tissue culture medium was monitored by absorbance at 490 nM on a Spectramax plate reader using Softmax Pro 4.6 software (Molecular Devices). Data were graphically displayed as percent DMSO control using GraphPad Prism 4.00, and $IC_{50}$ curves were fitted using a non-linear regression model with a sigmoidal dose response.

Results

Table 4 demonstrates that the compound of Example 1 can inhibit proliferation of the feline lymphoid cell line MYA-1 that is dependent on IL-2 for proliferation, but not an IL-2 independent line (FETJ). The compound of formula IA or its salt can also inhibit proliferation of canine nodal tissue obtained from dogs diagnoses with T- or B-cell lymphoma. These results suggest a JAK inhibitor may be effective in treating canine and feline lymphomas.

TABLE 4

| Species | Cell Line or Lymph Node | Description | Stimulant in Culture Medium | IC50 (nM) |
| --- | --- | --- | --- | --- |
| Feline | MYA-1 | Lymphoid line | | 122 (n = 2) |
| Feline | FETj | Lymphoid line | | >1000 |
| Canine | MSU LN 8 | De novo T-cell lymphoma | LPS + ConA | 357 |
| Canine | MSU LN 8 | De novo T-cell lymphoma | SAC + IL-2 | 38 |
| Canine | MSU LN 9 | De novo B-cell lymphoma | LPS + ConA | 147 |
| Canine | MSU LN 9 | De novo B-cell lymphoma | SAC + IL-2 | 100 |
| Canine | MSU LN 10 | Chemotherapy resistant B-cell lymphoma- | LPS + ConA | 687 |
| Canine | MSU LN 11 | De novo B-cell lymphoma | LPS + ConA | 64 |

What is claimed is:

1. A method for treating asthma and other obstructive airway diseases selected from the group consisting of chronic asthma, inveterate asthma, late asthma, airway hyper-responsiveness bronchitis, bronchial asthma, allergic asthma, intrinsic asthma, extrinsic asthma, dust asthma, recurrent airway obstruction, and chronic obstruction pulmonary disease in a mammal comprising administering to a mammal in need thereof a therapeutically effective amount of a compound of formula I:

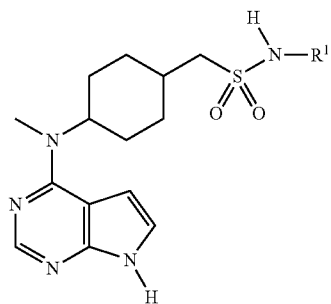

or a pharmaceutically acceptable salt thereof wherein $R^1$ is $C_{1-4}$alkyl optionally substituted with hydroxy.

2. The method of claim 1 wherein the therapeutically effective amount is from 0.01 mg/kg of body weight/day to 100 mg/kg of body weight/day.

3. The method of claim 1 wherein the therapeutically effective amount is from 0.1 mg/kg of body weight/day to 10 mg/kg of body weight/day.

4. The method of claim 1 wherein the mammal comprises companion animals.

5. The method of claim 4 wherein the companion animals are dogs, cats, and horses.

6. The method of claim 1 wherein the compound of formula I is administered orally, parenterally, or topically.

7. A method for treating autoimmune diseases, selected from rheumatoid arthritis and alopecia in a mammal comprising administering to a mammal in need thereof a therapeutically effective amount of a compound of formula I of claim 1.

8. A method for treating cancer selected from mast cell carcinoma, squamous cell carcinoma, lymphoma, and leukemia in a mammal comprising administering to a mammal in need thereof a therapeutically effective amount of a compound of formula I of claim 1.

9. A method for treating inflammatory bowel disease, eosinophilic gastroenteritis, and mastocytosis in a mammal comprising administering to a mammal in need thereof a therapeutically effective amount of a compound of formula I of claim 1.

10. The method of claim 1, 7, 8, or 9 wherein $R^1$ is methyl.

* * * * *

SEQUENCE LISTING

```
<160> NUMBER OF SEQ ID NOS: 2

<210> SEQ ID NO 1
<211> LENGTH: 14
<212> TYPE: PRT
<213> ORGANISM: Artificial Sequence
<220> FEATURE:
<223> OTHER INFORMATION: JAKtide peptide

<400> SEQUENCE: 1

Lys Gly Gly Glu Glu Glu Glu Tyr Phe Glu Leu Val Lys Lys
1               5                   10

<210> SEQ ID NO 2
<211> LENGTH: 13
<212> TYPE: PRT
<213> ORGANISM: Artificial Sequence
<220> FEATURE:
<223> OTHER INFORMATION: IRS-1 peptide

<400> SEQUENCE: 2

Lys Lys Ser Arg Gly Asp Tyr Met Thr Met Gln Ile Gly
1               5                   10
```